(12) United States Patent
Baldi et al.

(10) Patent No.: US 8,816,107 B2
(45) Date of Patent: *Aug. 26, 2014

(54) FUNCTIONALISED NANOPARTICLES, THEIR PRODUCTION AND USE

(75) Inventors: Giovanni Baldi, Montespertoli (IT); Alfredo Ricci, Bologna (IT); Mauro Comes Franchini, San Lazzaro di Savena (IT); Daniele Bonacchi, Pistoia (IT); Marco Bitossi, Montelupo Fiorentino (IT)

(73) Assignee: Colorobbia Italia S.p.A., Sovigliana-Vinci (IT)

(*) Notice: Subject to any disclaimer, the term of this patent is extended or adjusted under 35 U.S.C. 154(b) by 727 days.

This patent is subject to a terminal disclaimer.

(21) Appl. No.: 12/087,304

(22) PCT Filed: Jan. 3, 2007

(86) PCT No.: PCT/EP2007/050036
§ 371 (c)(1),
(2), (4) Date: Jul. 1, 2008

(87) PCT Pub. No.: WO2007/077240
PCT Pub. Date: Jul. 12, 2007

(65) Prior Publication Data
US 2009/0054555 A1 Feb. 26, 2009

(30) Foreign Application Priority Data
Jan. 4, 2006 (IT) .................. FI2006A0006

(51) Int. Cl.
*C07C 259/06* (2006.01)
*C07F 9/38* (2006.01)

(52) U.S. Cl.
CPC ........... *C07C 259/06* (2013.01); *C07B 2200/11* (2013.01); *C07F 9/3808* (2013.01)
USPC .............. 554/74; 554/71; 554/111; 562/621; 556/148

(58) Field of Classification Search
USPC .................... 427/127, 213.3, 215, 217, 220; 428/357, 402.24, 403; 523/200
See application file for complete search history.

(56) References Cited

U.S. PATENT DOCUMENTS

| | | | | |
|---|---|---|---|---|
| 2,279,560 A | * | 4/1942 | Dietrich | 508/548 |
| 3,367,959 A | * | 2/1968 | Fetscher et al. | 560/168 |
| 5,318,838 A | * | 6/1994 | Matsufuji et al. | 428/328 |
| 5,422,193 A | * | 6/1995 | Nakamura et al. | 428/844.5 |
| 6,423,296 B1 | * | 7/2002 | Gunther et al. | 424/9.322 |
| 2004/0059156 A1 | * | 3/2004 | Hughes | 562/621 |
| 2005/0181970 A1 | * | 8/2005 | Huang et al. | 510/507 |
| 2007/0248678 A1 | * | 10/2007 | Woo et al. | 424/489 |

FOREIGN PATENT DOCUMENTS

| | | | |
|---|---|---|---|
| JP | 2006-104051 | * 4/2006 | |
| WO | 2004108116 A2 | 12/2004 | |
| WO | WO2006080895 | 8/2006 | ............... C07F 1/10 |

OTHER PUBLICATIONS

Sun, J. Am. Chem. Soc. 2004, 126, 273-279.*
Folkers, Langmuir, 1995, 11, 813-824.*
Pawsey, Langmuir, 2002, 18, 5205-5212.*
Bagaria, Langmuir, 2006, 22, 7732-7737.*
Aronoff, Yael G. et al., "Stabilization of Self-Assembled Monolayers of Carboxylic Acids on Native Oxides of Metals," *J. Am. Chem. Soc.*, 1997, vol. 119 (2) pp. 259-262.
Folkers, John P. et al., "Self-Assembled Monolayers of Long-Chain Hydroxamic Acids on the Native Oxide of Metals," *Langmuir*, 1995, vol. 11 (3) pp. 813-824.
Pawsey, Shane et al., "Self-Assembly of Carboxyalkylphosphonic Acids on Metal Oxide Powders," *Langmuir*, 2002, vol. 18(13)pp. 5205-5212.
Yee et al. "*Self-Assembled Monolayers of Alkanesulfonic and -phosphonic Acids on Amorphous Iron Oxide Nanoparticles*", Langmuir, vol. 15(21), Sep. 16, 1999, pp. 7111-7115.
International Search Report dated Sep. 4, 2007 based on PCT application No. PCT/EP2007/050036.
English Translation of Korean Search Report dated Apr. 26, 2013, from corresponding Korean Application No. 10-2008-7019077, 8 pages.

* cited by examiner

*Primary Examiner* — Robert C Boyle
(74) *Attorney, Agent, or Firm* — Ohlandt Greeley Ruggiero & Perle L.L.P.

(57) ABSTRACT

Stable complexes are described, formed by mono- and difunctional compounds bound to nanoparticles composed of various types of transition metal oxides and of metals useful in the production processes of different types of new materials (such as for example some types of hydrophile plastics, fibers); processes for the production of the complexes are also described.

4 Claims, 4 Drawing Sheets

● = nanoparticle

↷ = monofunctionalised binder (▼ = carboxylic, hydroxamic, phosphate, thiolic group)

↶ = bifunctionalised binder (▼=carboxylic, hydroxamic, phosphate, thiolic group; ● = carboxylic, aminic, hydroxylic group)

⟋▱ = polymer or functional molecules (U= carboxylic acid, aminic, hydroxylic acrylamide group)

A

B

A

B

FUNCTIONALISED NANOPARTICLES, THEIR PRODUCTION AND USE

BACKGROUND

1. Field of the Invention

The present disclosure concerns the field of functionalised nanoparticles, their production and use.

2. Discussion of the Background Art

It is known how some organic molecules are able to be absorbed on surfaces of solid inorganic materials and this property has been widely used to the extent that entire classes of technologically important compounds have been formed, such as dispersants and "wetting agents".

Some of these molecules not only are absorbed by the surface involved but also contribute to the formation of compact structures which may profoundly alter its properties.

Typical examples of organic molecules of the above type (defined here below as binders) are simple monofunctionalised aliphatic compounds such as thiols, sodium dodecyl phosphate, cetyl trimethyl ammonium bromide, various aliphatic phosphates and the phosphonic, carboxylic and hydroxamic acids.

Interaction usually occurs between the single functional group and the metallic inorganic surface leaving thereby free a simple aliphatic chain that is not able to interact in any way whit other functional molecules.

The affinity between the organic molecules and the surfaces depends on the chemical nature of each: these interactions have been studied for some very well-known cases, however a complete understanding of the affinities of the various binders with the surfaces of nanoparticles is still being discussed in the academic fields, since the results are often contradictory.

It is also known that nanoparticles are materials with dimensions smaller than 500 nm, or according to some authors smaller than 100 nm, which may form a stable dispersion in liquids if there is a repulsion potential between the individual units. No precipitation is observed in a dispersion because the intrinsic movement due to temperature prevents their being deposited by the effect of gravity. The potential of interaction between two particles depends above all on the surface status of the nanoparticle; this may be varied by absorption or by chemical binding with other molecular or ionic species present in the solution.

Some complexes composed of nanoparticles and monofunctional binders of the type mentioned above are known [see, for example, Aronoff, Y. G. et al. *J. Am. Chem. Soc.* 1997, 119, 259-262. Heimer, T. A.; D'Arcangelis et al. *Langmuir,* 2002, 18, 5205-5212; Yee, C. et al. *Langmuir,* 1999, 15, 7111-7115; Folkers, J. et al. *Langmuir,* 1995, 11, 813-824] but they present various disadvantages.

Besides the scarcity of materials and binders studied, the above-mentioned products are not soluble in a hydroalcoholic environment, a condition which is very important for biomedical and pharmacological applications. Moreover the simple aliphatic chain which remains free is absolutely not able to interact with the functionalities usually present in bioactive molecules.

On the basis of the above, it is clearly important to have complexes formed of nanoparticles and of functionalised binders which make them suitable for the various desired purposes, overcoming the above-mentioned disadvantages.

SUMMARY

Stable complexes can be obtained by binding nanoparticles of various types of transition metal oxides with mono- and di-functional compounds.

DETAILED DESCRIPTION OF THE PREFERRED EMBODIMENTS

Figure 1:
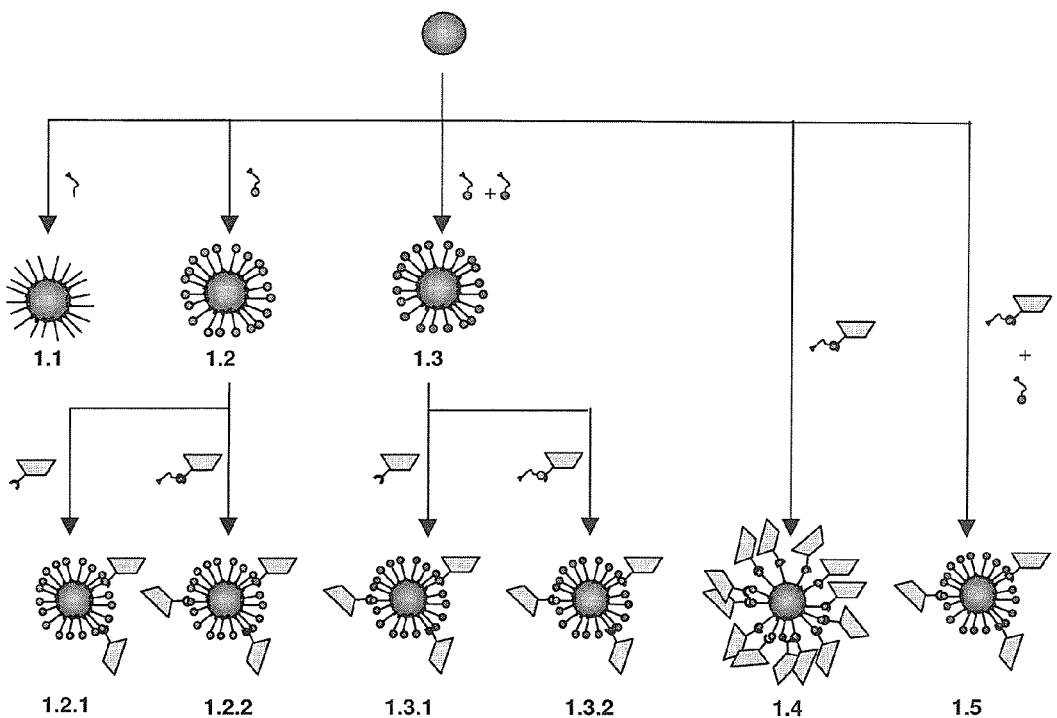
FIG. 1 schematically illustrates the preparation processes of the complexes composed of nanoparticles with the previously described difunctionalised binders and the subsequent reactions of said complexes with biopolymers, molecules (cyclodextrins, antibodies, etc.) and proteins.
Figure 2:
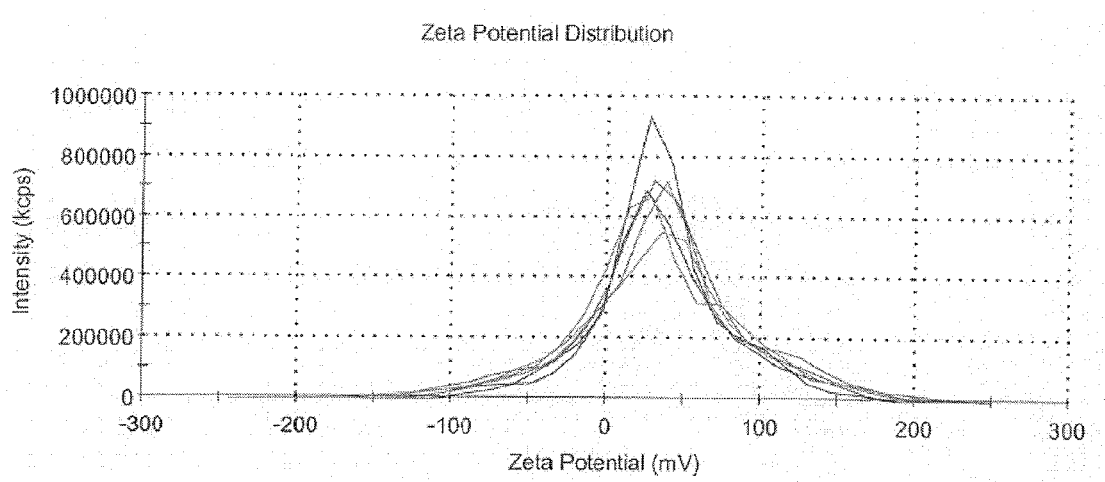
FIGS. 2a and 2b show the Z-potential of the suspension in ethanol before and after functionalisation.
Figure 2:
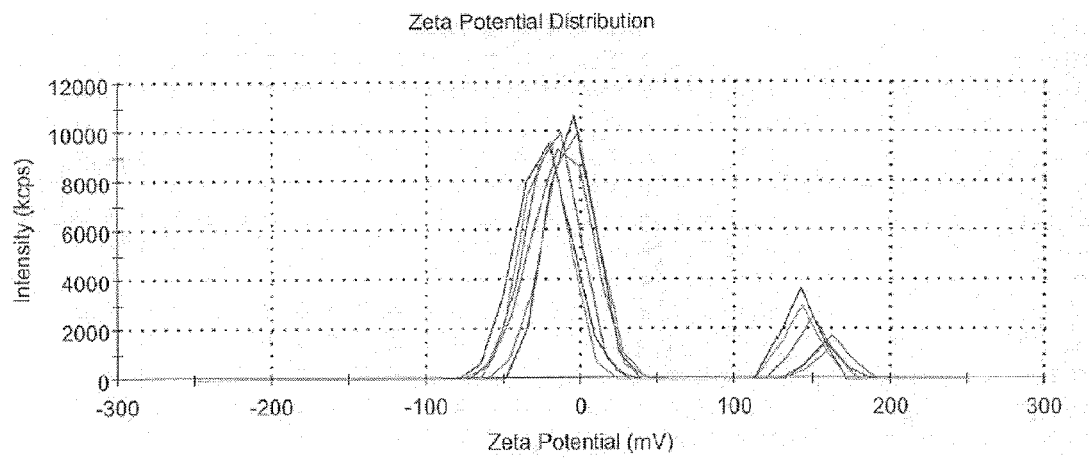
Figure 3:
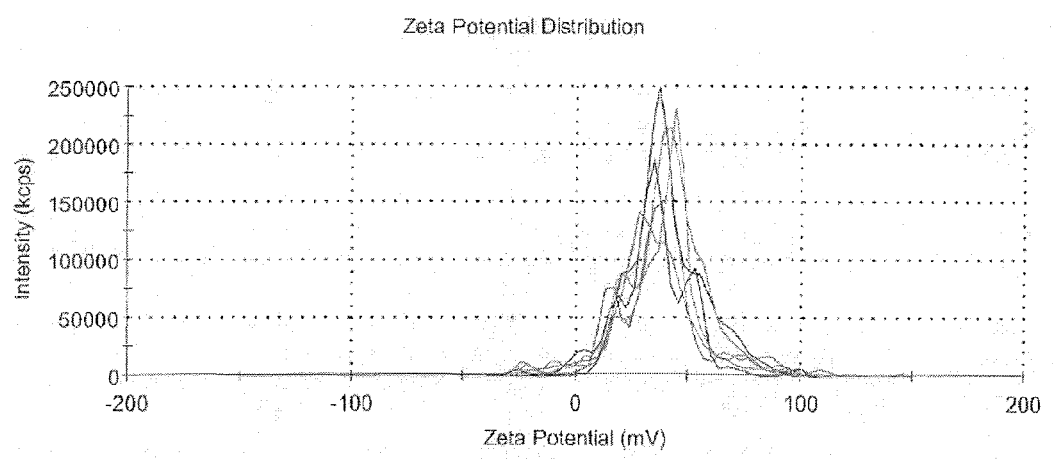
FIGS. 3a and 3b show the Z-potential of the suspension in water before and after functionalisation.
Figure 3:
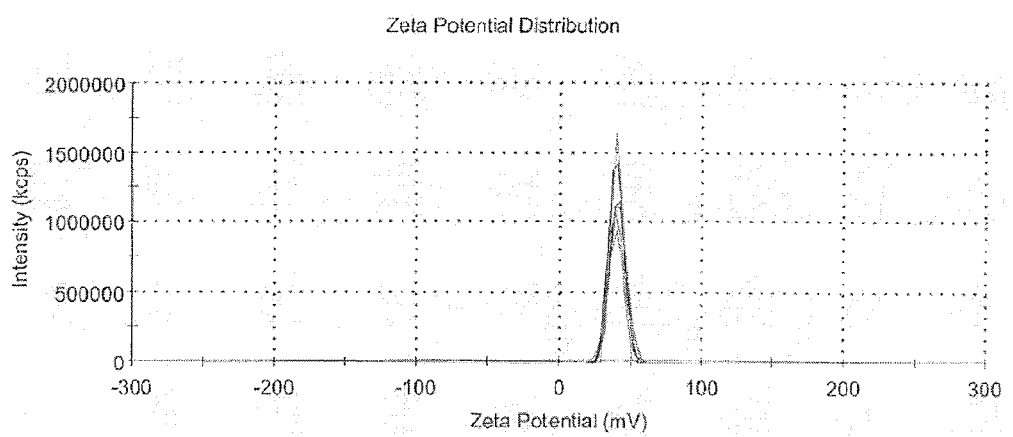
Figure 4:
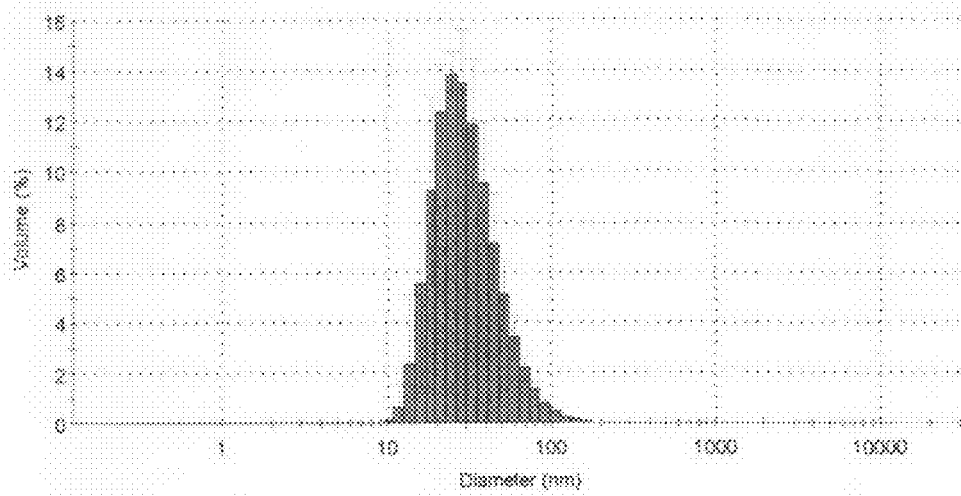
FIG. 4 is a graph plotting volume versus diameter for Cobalt ferrite/hydroxamic acid nanoparticle complex.

It has now surprisingly been found that mono- and difunctional compounds are able to bind with nanoparticles composed of various types of transition metal oxides and of metals forming stable complexes.

Monofunctional binders have the advantage of being soluble in non polar solvents such as alkanes and they can therefore be used in some types of processes compatible with solvents of this type (hydrophobic plastics, some types of synthetic fibres, etc.).

In the case of difunctional binders the added functional group (which does not interact with the inorganic metallic surface) leads to modifications of the solubility of the nanoparticle in the liquid medium, making the nanoparticle usable in production processes of various types of new materials (some types of hydrophile plastics, fibres); it also allows chemical interactions with further complex units such as biopolymers, cyclodextrins, antibodies and drugs for use in the pharmaceutical and diagnostic field.

Moreover the use of difunctional compounds allows complexes of nanoparticles and binder to be obtained in which total and compact covering of the nanoparticle is achieved without significant alterations of the properties that depend on it (for example magnetic or optical properties).

Among the other advantages it must be considered that, thanks to the total coverage of their surface obtained using the above binders, the nanoparticles are non toxic.

According to the present disclosure, the term monofunctional and difunctional compounds means thiols, carboxylic acids, hydroxamic acids, esters, phosphoric acids (or the salts thereof) with an aliphatic chain which, in the specific case of difunctional binders, have a second functional group in the end position (called ω). Preferably said second functional group is chosen in the group composed of: OH, $NH_2$, COOH, $COOR_3$ wherein $R_3$ is as hereinafter defined.

More particularly, mono- and difunctional compounds according to the present disclosure are compounds with the general formula:

$$R_1-(CH_2)_n-R_2$$

in which:
n is an integer between 2 and 20;
$R_1$ is chosen in the group composed of: H, OH, $NH_2$, COOH, $COOR_3$;

$R_2$ is chosen among: CONHOH, CONHOR$_3$, PO(OH)$_2$, PO(OH)(OR$_3$), COOH, COOR$_3$, SH, SR$_3$;

$R_3$ is an alkaline metal, preferably K, Na or Li, or a protective organic agent.

The mono- or difunctional compounds as defined above are known or may be prepared according to known processes.

In the case of monofunctional compounds, it is a case of transforming the compound containing the carboxylic functionality (available on the market) into the corresponding product in which the carboxylic group is replaced by a hydroxamic group according to well known procedures in the literature, or a derived halogen in a phosphoric group, in this case too according to known synthetic procedures.

For difunctional compounds, the preparation process normally contemplates the start of synthesis from a simple difunctional compound available on the market (for example carboxylic acids or omega-functionalised alcohols), the protection of the functional group in ω position, and finally the activation of the carboxylic (or alcoholic) function for the subsequent insertion of hydroxamic or phosphoric functionality.

According to the present disclosure, the term nanoparticles means particles with dimensions between 1 and 200 nm.

Particularly preferred, according to the disclosure, are nanoparticles composed of: metals and metallic oxides belonging to the series of transition metals, in particular compounds with general formula $M^{II}M^{III}{}_2O_4$ with $M^{II}$=Co, Ni, Fe, Zn, Mn and $M^{III}$=Fe$^{III}$, Co, Al. Oxides of the maghemite type Fe$_2$O$_3$. Specifically: cobalt ferrite CoFe$_2$O$_4$, magnetite FeFe$_2$O$_4$, maghemite γ-Fe$_2$O$_3$. Metallic particles composed of metallic Fe$^0$ and Co$^0$ and their alloys, even with noble metals.

Complexes of nanoparticles and binders are obtained by making the mono- or difunctional derivatives as described above react with the nanoparticles as defined above so as to cover their free surface totally.

The preparation process is carried out by making a dispersion of nanoparticles in an organic solvent (for example ethylene glycol) react with the preferred binder, keeping it stirring at a reduced temperature for a few hours.

The product is then precipitated, for example with acetone, centrifuged, separated and if necessary purified by redispersion in a suitable solvent and reprecipitation.

The coverage and the reaction achieved were assessed with different experimental techniques including DSC-TG thermogravimetry, FT-IR spectroscopy, elementary analysis and Dynamic Light Scattering (DLS).

The effects of surface functionalisation on the magnetic properties of the product were also assessed.

The functionalised nanoparticles thus produced can be used in processes which require a specific hydrophobic/hydrophilic behaviour such as the production of plastics (for example polyethylene or polyester plastics) or synthetic fibres (e.g. nylon) and natural fibres (e.g. cotton).

The process of synthesis consists of establishing a bond between a nanoparticle and a monofunctional binder of the palmitic acid type (see example 1).

Moreover the nanoparticles treated with bifunctional binders may be further modified by attacking particular molecules to the functional group (for example cyclodextrins, folic acid, antibodies and drugs), proteins or polymers (for example polyamidoamine) so as to combine the properties of the particle (magnetism) with the properties of the molecule or of the polymer (biocompatibility, invisibility to the immune system) or of the proteins.

The magnetic properties may be used to constitute general and selective contrasting agents, for magnetic resonance analysis, or combined with drugs to constitute vehiculation systems the release of which is regulated by the heating of the particles by hyperthermic effect.

In general it may be said that for the assembly of the nanoparicle/difunctional binder complex, which we shall refer to below as functionalised nanoparticle, -molecule, polymer or protein as defined above, the following criteria may be followed.

a) The functionalised nanoparticles which present amines as external functionality may be bound to molecules, polymers or proteins as defined above which may present one of the following functionalities: carboxylic acids, aldehydes and acryl amides.

b) The functionalised nanoparticles which present carboxylic acids as external functionality may be bound to biopolymers, proteins or molecules (cyclodextrins, folic acid, antibodies, drugs) which in turn may present one of the following functionalities: alcohols, amines and thiols.

c) The functionalised nanoparticles which present oxydril groups as external functionality may be bound to biopolymers, proteins or molecules (cyclodextrins, folic acid, antibodies, drugs) which in turn may present one of the following functionalities: carboxylic acids.

As may be seen, the compounds formed by the nanoparticle/difunctional binder complexes and the functional molecules as described above may be obtained following various preparation processes.

Processes

Process A

Functionalisation of the nanoparticle with simple difunctional binders such as for example ω-hydroxy-, ω-carboxy- and ω-amino-carboxylic acids; ω-hydroxy-, ω-carboxy- and ω-amino-hydroxamic acids; ω-hydroxy-, ω-carboxy- and ω-amino-phosphoric acids; ω-hydroxy-, ω-carboxy- and ω-amino-thiols. Subsequent binding of the bifunctionalised particles with molecules, proteins or polymers with difunctional binders.

Process B

Anchoring of the molecules, polymers or modified proteins with binders to the functionalised nanoparticles by means of the exchange of binders.

Process C

Identical to process A apart from the functionalisation of the nanoparticle with mixtures of difunctionalised binders.

Process D

Identical to process B apart from the functionalisation of the nanoparticle with mixtures of difunctionalised binders.

Process E

Direct functionalisation of the nanoparticle with molecules, polymers or proteins previously bound to a suitable difunctional binder.

Process F

Functionalisation of the nanoparticle with mixtures containing molecules, polymers or proteins already bound to a suitable difunctional binder and a different difunctional binder.

To illustrate the disclosure better, below are given some specific examples of the preparation of the binders, of the complexes, and of their subsequent functionalisation.

Cobalt Ferrite/Hydroxamic Acid Nanoparticle Complex (Product Diagram 1.1)

A quantity of 10 g of a dispersion in diethylene glycol containing 3% in weight of nanoparticles, for example cobalt ferrite, with diameter 5 nm is added to 0.3 g of hydroxamic acid added after solubilisation in 20 g of hexane and the whole is kept stirring at room temperature for 2 hours. Extraction is then performed with 40 g hexane for 30 minutes. When stirring is interrupted the separation of the two apolar and polar phases is observed, the apolar (upper) phase takes on a strong black colour indicating the presence of cobalt ferrite, while the lower polar phase is transparent. The two phases are separated and the phase containing the nanoparticles can then be washed with washes having a base of water or water/ethanol 1:1. To isolate the coated particles the solvent may be removed by evaporation by means of heating or by vacuum. Alternatively, before extraction the product may be separated by centrifugation and then redispersed in the suitable solvent.

Experimental Data:
IR: 3394; 2915.12; 2856.08; 1594.20; 1122.58; 1060.10.
TG: Loss at 500° C., 26%
DLS:

Example 1

Synthesis of 12-amino-N-hydroxy dodecanamide

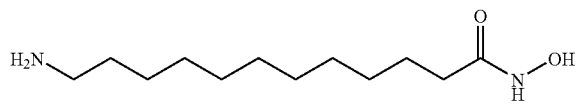 [SMILES: NCCCCCCCCCCCC(=O)NO]

a) Synthesis of 12-amino-(tert-butoxycarbonyl)dodecanoic acid

In a 250 ml Sovirel two-neck flask with a magnetic anchor, with perforable septum and tap for argon, the 12-aminododecanoic acid available on the market (5.2 g, 25.8 mmol) is dissolved in dioxane (20 mL) and Boc$_2$O is added (6.5 mL, 28 mmol). The system is brought to 0° C. and the NaOH 2N (13.2 mL) is dripped slowly. The solution is allowed to react under reflux conditions for 24 hours. Distilled water (60 mL) is added and extraction is performed with Et$_2$O (2×30 mL). The aqueous phase is acidified with citric acid (25% w/w) to pH=5. It is extracted with EtOAc (3×50) and the combined tragic fractions are anhydrified with MgSO$_4$ and concentrated with a Rotavapor and with a high vacuum pump. 6.0 g of 12-amino-(tert-butoxycarbonyl) dodecanoic acid are obtained (Yield=73%).
m.p.=80-82° C.
Spectroscopic Data:
IR: 3365, 2919, 2853, 1727, 1688, 1520, 1469, 1365, 1246, 1172, 946.
$^1$H-NMR (400 MHz, CD$_3$OD): 1.35 (s, 9H), 1.40-1.60 (m, 18H), 2.35 (t, J=7.0 Hz, 2H), 3.00 (t, J=6.6 Hz, 2H), 4.80 (brs, 1H).
$^{13}$C-NMR (100.2 MHz, CD$_3$OD): 24.9, 26.7, 27.7, 29.1, 29.3, 29.4 (2CH2), 29.48, 29.5, 29.8, 33.8, 40.2, 78.6, 157.3, 176.4.
MS: 315 (M$^+$)

b) Synthesis of dicyclohexyl ammonium salt of 12-amino-(tert-butoxycarbonyl)dodecanoic acid Dicyclohexyl amine (3.92 mL, 19.7 mmol) is added to a suspension of 12-amino-(tert-butoxycarbonyl)dodecanoic acid (5.8 g, 18.4 mmol) in MeOH (20 mL). The resulting suspension is kept stirring for 10 minutes at room temperature. The solvent is eliminated under a vacuum and 9.1 g of product are obtained (Yield=100%) as a powdery white solid which is then used without any purification.

c) Synthesis of tert-butyl 12-(benzyloxyamino)-12-oxododecyl carbamate

Dicyclohexyl ammonium salt of 12-amino-(tert-butoxycarbonyl)dodecanoic acid (9.1 g, 18.4 mmol) is placed in a 100 ml Sovirel two-neck flask with a magnetic anchor, with perforable septum and tap for argon and pyridine (1.50 mL, 15.2 mmol) and dichloromethane (18 mL) are added.
Thienyl chloride (22.1 mmol, 1.62 mL) is added with a syringe and left to react for 5 minutes at room temperature. In the meantime, in another two-neck flask, benzyloxyamine chlorohydrate (2.9 g, 18.4 mmol) is weighed and 4-dimethylamine pyridine (DIMAP, 3.6 g, 3.0 mmol) and dichloromethane (36 mL) are added.
This solution is dripped with a syringe into the first flask and the whole is left stirring at room temperature for 1 hour. The solvent is eliminated with the Rotavapor and purification is carried out with column chromatography on silica gel (eluant ethyl acetate/petroleum ether 1/1) which leads to the isolation of 3.8 g (Yield=50%) of product as a yellow-white solid.
m.p.=68-73° C.
Spectroscopic Data:
IR: 3346, 3298, 2922, 2851, 1682, 1657, 1540, 1356, 1269, 1254, 1171.
$^1$H-NMR (400 MHz, CDCl$_3$): 1.05-1.10 (m, 16H), 1.40 (s, 9H), 1.40-1.55 (m, 2H), 2.00 (brs, 2H), 3.00-3.10 (m, 2H), 4.80 (brs, 1H), 4.90 (s, 2H), 7.25-7.35 (m, 5H), 9.25 (brs, 1H).
$^{13}$C-NMR (75.3 MHz, CDCl$_3$): 25.2, 26.4, 28.1, 28.8, 28.9, 29.1, 29.2, 29.7, 32.7, 40.3, 77.5, 78.6, 128.0, 128.7 (2ArCH), 135.3, 155.8, 170.1
MS: 420 (M$^+$)

d) Synthesis of 12-amino-N-(benzyloxy)dodecanamide

Chloroform (30 mL) is added to a single-neck flask under an inert atmosphere containing tert-butyl 12-(benzyloxyamine)-12-oxododecyl carbamate (3.14 g, 7.5 mmol). Trifluoroacetic acid (5.6 mL, 7.5 mmol) is dripped slowly and left stirring at room temperature for 1 hour. The solvent is eliminated with the Rotavapor and concentrated ammonia is added up to pH=9. Distilled water (30 mL) and chloroform (30 mL) are added. Extraction is performed with chloroform (3×25 mL) and the organic phases are anhydrified on magnesium sulphate. It is filtered and the solvent is eliminated to obtain 2.0 g (Yield=85%) of product as a yellowish solid.
m.p.=76-78° C.
Spectroscopic Data:
IR: 3357, 3225, 2907, 2841, 1657, 1553, 1369, 1203, 1057.
$^1$H-NMR (400 MHz, CDCl$_3$): 1.00-1.40 (m, 16H), 1.45-1.55 (brs, 2H), 2.00 (brs, 2H), 2.45 (brs, 2H), 4.80-5.00 (brm, 5H), 7.20-7.40 (m, 5H).
$^{13}$C-NMR (75.3 MHz, CDCl$_3$): 25.3, 26.5, 28.9, 29.0, 29.1, 29.2, 29.24, 32.7, 32.9, 41.5, 77.5, 128.2, 129.0 (2ArCH), 135.7, 170.7.
MS: 320 (M$^+$)

e) Synthesis of 12-amino-N-hydroxy dodecanamide

Hydrogenation is carried out with hydrogen in a Parr reactor. Pd—C 120 mg, 12-amino-N-(benzyloxy)dodecanamide (1.0 g, 2.4 mmol) and ethanol (40 mL) are put into the reactor. It is advisable to heat the product in the ethanol to 50° C. first in an Erlenmeyer flask. Hydrogenation lasts 30 hours, after which filtration is carried out on a porous septum with a layer of celite, washing the septum several times with ethanol. The solution is concentrated in the Rotovapor and in the high vacuum pump to give 12-amino-N-hydroxy dodecanamide as a white solid (500 mg, Yield=66%).

m.p.=: 112-116° C.

Spectroscopic Data:

IR: 3247, 2973, 2856, 1712, 1635, 1465, 1207, 1155, 1041.

$^1$H-NMR (400 MHz, CDCl$_3$): 1.10-1.60 (m, 18H), 2.0 (brt, 2H), 2.70-2.75 (m, 4H), 6.80 (brs, 1H), 7.40 (brs, 1H).

$^{13}$C-NMR (75.3 MHz, CDCl$_3$): Interval CH$_2$ 25.9-33.0, 41.8, 169.8.

MS: 230 (M$^+$).

Following the same synthetic protocol, N-12-dihydroxy dodecanamide can be obtained from 12-hydroxy dodecanoic acid.

HO~~~~~~~~~~C(O)NHOH

Example 2

Synthesis of potassium hydrogen-12-aminododecyl phosphonate

H$_2$N~~~~~~~~~~~~PO(OH)(OK)

a) Synthesis of ter-butyl 12-hydroxy dodecylcarbamate

In a 100 mL two-neck flask with a reflux condenser, magnetic anchor, and placed under a static head of nitrogen 12-amino-1-dodecanol chlorohydrate (3.34 g, 14.1 mmol) is weighed, and pyridine (40 mL), $^i$Pr$_2$Net (2.45 mL, 14.1 mmol) and Boc$_2$O (3.24 mL, 14.1 mmol) are added. This is left stirring at 70° C. for 60 hours, It is concentrated in the Rotovapor and the high vacuum pump and the product is purified with column chromatography on silica gel with an eluant mixture of petroleum ether/ethyl acetate 1/1. 3.1 g of ter-butyl 12-hydroxy dodecylcarbamate are isolated as a white solid for a yield of 73%.

m.p.=78° C.

Spectroscopic Data:

IR: 3424, 3370, 2920, 2852, 1686, 1523, 1172, 1058.

$^1$H-NMR (400 MHz, CDCl$_3$): 1.20-1.30 (brs, 20H), 1.40 (brs, 9H), 3.15 (brs, 2H), 3.6 (t, J=8.5 Hz, 2H), 4.4 (brs, 1H).

$^{13}$C-NMR (75.3 MHz, CDCl$_3$): 24.8, 26.7, 27.6, 29.0, 29.2 (2CH$_2$), 29.5, 29.6, 29.7, 29.73, 33.7, 40.1, 78.9, 157.1

MS: 301 (M$^+$)

b) Synthesis of ter-butyl 12-bromo dodecylcarbamate

In a 250 mL two-neck flask, with reflux condenser and magnetic anchor and under a static head of nitrogen the ter-butyl 12-hydroxy dodecylcarbamate (3.07 g, 10.2 mmol) is dissolved in dichloromethane (75 mL). PPh$_3$ (2.94 g, 11.2 mmol) and NBS (2.42 g, 10.7 mmol) are added. The mixture is left stirring under reflux conditions for 24 hours. It is concentrated in the Rotavapor and the product is purified with column chromatography on silica gel with an eluant mixture of petroleum ether/ethyl acetate 3/1. 2.9 g of ter-butyl 12-bromo dodecylcarbamate are isolated as a low-melting white solid for a yield of 78%.

m.p.=42-44° C.

Spectroscopic Data:

IR: 3421, 3366, 2924, 2853, 1688, 1521, 1170, 1061.

$^1$H-NMR (400 MHz, CDCl$_3$): 1.10-1.20 (brs, 20H), 1.35 (brs, 9H), 3.05 (brs, 2H), 3.60 (t, J=6.0 Hz, 2H), 4.80 (brs, 1H).

$^{13}$C-NMR (100.4 MHz, CDCl$_3$): 26.4, 27.8, 28.1, 28.4, 28.9, 29.1, 29.15, 29.2, 29.7, 32.5, 33.4, 40.2, 78.2, 155.2

MS: 363 (M$^+$).

c) Synthesis of ter-butyl 12-(diethoxyphosphoryl)dodecylcarbamate

In a single-neck flask with a reflux condenser, ter-butyl 12-bromo dodecilcarbamate (2.39 g, 6.6 mmol) is weighed and triethyl phosphate (2.25 mL, 13.1 mmol) is added. The reaction mixture is brought to 150° C. and left stirring under a static head of nitrogen. After 18 hours the single-neck flask is attached to the high vacuum pump to eliminate the volatile products and the resulting dense oil is directly loaded with column chromatography on silica gel. It is eluted with a mixture of ethyl acetate/petroleum ether 1/1 which leads to the isolation of 0.4 g of ter-butyl 12-(diethoxyphosphoryl)dodecylcarbamate (yield 14%) as a colourless oil.

Spectroscopic Data:

IR: 3420, 3371, 2922, 2850, 1687, 1218, 1060.

$^1$H-NMR (400 MHz, CDCl$_3$): 1.20-1.45 (m+t, J=7.0 Hz, 35H), 1.55-1.60 (bm, 2H), 3.05 (brq, 2H), 3.90-4.15 (m, 4H).

$^{13}$C-NMR (75.3 MHz, CDCl$_3$): 15.6, 24.9-29.8 (10CH$_2$+ t-Bu), 40.0, 61.2, 65.2, 78.3, 155.6.

MS: 421 (M$^+$).

d) Potassium hydrogen-12-amino dodecylphosphonate

In a single-neck flask with a reflux condenser, ter-butyl 12-(diethoxyphosphoryl)dodecylcarbamate (0.35 g, 8.3 mmol) is weighed and concentrated HCl (1.5 mL) is added. The temperature is brought to 100° C., and it is left stirring under a static head of nitrogen. After 18 hours it is concentrated in the high vacuum pump, obtaining a light brown rubbery solid.

Spectroscopic Data:

IR: 3431, 2900, 2841, 1631, 1470, 1172, 1045, 952.

$^1$H-NMR (400 MHz, CDCl$_3$): widened signals: (1.0-1.80, m), brs 2.80, brs 3.40.

$^{13}$C-NMR (100.4 MHz, CDCl$_3$): 23.0-28.8 (overlapping signals), 31.2, 33.4.

MS: 265 (M$^+$).

Example 3

Synthesis of potassium hydrogen-12-hydroxy dodecylphosphonate

HO~~~~~~~~~~~~P(O)(OH)(OK)

a) Synthesis of 12-Bromododecyl benzoate

In a 100 mL two-neck flask under a static head of nitrogen 12-bromo-dodecanol (5.0 g, 18.9 mmol) is weighed, pyridine (25 mL) is added and the whole is brought to 0° C. with an external bath of ice and salt. Benzoyl chloride is dripped slowly and, when adding is finished, the ice bath is removed and the whole is left stirring at room temperature. After 18 hours ethyl acetate (100 mL) and distilled water (100 mL) are added. The organic phase is washed 3 times with distilled water (3×50 mL) and anhydrified on anhydrous sodium sulphate. It is filtered under a vacuum and the solvent is eliminated in the Rotovapor and in the high vacuum pump. The product is purified with column chromatography on silica gel with an eluant mixture of petroleum ether/ethylic ether 5/1. 4.5 g of 12-bromododecyl benzoate are isolated as a colourless oil with a yield of 65%.

Alternatively, after 18 hours ethyl acetate (100 mL) is added to the reaction mixture which is then washed with a saturated aqueous solution of copper sulphate (3×80 mL) to eliminate the pyridine, in this way the yield rises to 90% without column chromatography and the product is used directly in the next stage.

Spectroscopic Data:
IR: 2926, 2853, 1716, 1269, 1109.
$^1$H-NMR (400 MHz, CDCl$_3$): 1.10-1.60 (m, 16H), 1.60-1.80 (m, 4H), 3.55 (t, J=6.8 Hz, 2H), 4.25 (t, J=6.8 Hz, 2H), 7.30-7.35 (m, 3H), 8.00-8.05 (m, 2H) ppm.
$^{13}$C-NMR (75.3 MHz, CDCl$_3$): 25.8, 26.6, 28.5, 28.6-29.3 (6CH$_2$), 32.4, 44.8, 64.8, 128.0, 129.3, 130.3, 132.5, 166.3.
MS: 369 (M$^+$).

b) Synthesis of 12-Diethoxyphosphoryl benzoate

In a single-neck flask, with reflux condenser, 12-bromododecyl benzoate (4.25 g, 11.5 mmol) is weighed and triethyl phosphite (4.11 mL, 24 mmol) is added. The reaction mixture is brought to 150° C. and left stirring under a static head of nitrogen. After 24 hours the single-neck flask is attached to the high vacuum pump to eliminate the volatile products and the resulting dense oil is directly loaded with column chromatography on silica gel. It is eluted with a mixture of ethyl acetate/petroleum ether 1/1 which leads to the isolation of 4.0 g (yield 82%) of 12-diethoxyphosphoryl benzoate as a colourless oil.

Spectroscopic Data:
IR: 3663, 3425, 2927, 2844, 1721, 1218, 1064.
$^1$H-NMR (400 MHz, CDCl$_3$): 1.30 (t, J=7.0 Hz, 6H), 1.40-1.80 (m, 22H), 3.95-4.05 (m, 4H), 4.25 (t, J=6.0 Hz, 2H), 7.40-7.65 (m, 3H), 8.00-8.05 (m, 2H) ppm.
$^{13}$C-NMR (75.3 MHz, CDCl$_3$): 16.0, 22.6, 24.2-34.1 (10CH$_2$), 61.0, 65.3, 128.2, 129.4, 131.4, 167.1.
MS: 426 (M$^+$).

c) Synthesis of potassium hydrogen-12-hydroxy dodecylphosphonate

In a single-neck flask with a reflux condenser, 12-diethoxyphosphoryl benzoate (4.0 g, 9.3 mmol) is weighed and concentrated HCl (10 mL) is added. The mixture is brought to a temperature of 100° C. and left stirring under a static head of nitrogen. After 72 hours ethyl acetate (80 mL) and distilled water (40 mL) are added. Separation is carried out in a separating funnel and the water is extracted three more times with ethyl acetate (3×50 mL). The combined organic phases are washed with a saturated solution of NaCl, anhydrified with anhydrous sodium sulphate and concentrated in the Rotovapor and in the high vacuum pump. Column chromatography is performed on silica gel with eluant petroleum ether/ethyl acetate 1/1. The benzoic acid subproduct is isolated first and then, after changing to pure methanol as eluant, the product 12-benzyloxydodecyl phosphoric acid. Continuing column chromatography, the total hydrolysis product 12-hydroxydodecyl phosphoric acid is also isolated. The last two products (about 2.0 g) are kept together and used in the next stage.

The two isolated products are placed in a single-neck flask with a reflux condenser and methanol (50 mL), distilled water (20 mL) and potassium carbonate (13 mmol, 1.8 g) are added. The mixture is brought to 50° C. and is left stirring under a static head of nitrogen for 18 hours. The methanol is eliminated in the Rotovapor and extraction is carried out three times with ethyl ether (3×20 mL) to eliminate the methyl benzoate which has formed as a subproduct. 10% HCl is added to the aqueous solution up to an acid pH. A white solid precipitates, the water is eliminated in the Rotovapor and in the high vacuum pump. The solid obtained is dissolved in methanol and decanted to eliminate the potassium chloride.

m.p.=270-279° C.

Spectroscopic Data:
IR: 3357, 2917, 2850, 1467, 1233, 1162, 1010, 936.
$^1$H-NMR (400 MHz, D$_2$O): 1.10-1.90 (m, 22H), 3.40 (brs, 2H).
$^{13}$C-NMR (75.3 MHz, D$_2$O): 24.5, 25.3, 29.0-29.3 (7CH$_2$), 30.5, 31.7, 61.9.
MS: 266 (M$^+$).

The phosphoric acid thus obtained is treated with equimolar KOH and heated in methanol to obtain the corresponding potassium salt. 1.3 g of potassium salt of 12-hydroxy dodecylphosphonate is obtained, yield 57% (from 12-diethoxyphosphoryl benzoate) as a powdery white solid.

m.p.=336-348° C.

Spectroscopic Data:
IR: 3308, 2918, 2851, 2364, 1651, 1553, 1399, 1082, 977, 831.
$^1$H-NMR (400 MHz, CD$_3$OD): 1.20-1.85 (m, 22H), 3.50 (t, J=6.8 Hz, 2H)
$^{13}$C-NMR (75.3 MHz, CD$_3$OD): 22.9, 25.7, 29.1-29.5 (7CH$_2$), 30.7 (d, J=12 Hz), 61.8
MS: 265 (M$^-$), 39 (K$^+$)

Example 4

Synthesis of potassium hydrogen-13-ethoxy-13-oxamidecyl phosphonate

KOOC~~~~~~~~~PO(OH)(OK)

a) Synthesis of ethyl 12-hydroxydodecanoate

In a 100 mL two-neck flask with a reflux condenser and magnetic anchor, under a static flux of nitrogen, 12-hydroxydodecanoic acid (5.0 g, 23.2 mmol) is weighed, ethanol (20 mL) and acetyl chloride (1.62 mmol, 0.09 ml, 0.1 eq.) are added. The mixture is left stirring in reflux conditions for 24 hours. It is concentrated in the Rotovapor and in the high vacuum pump and the product is purified with column chromatography on silica gel with eluant mixture petroleum ether/ethyl acetate 5/4. 3.30 g of ethyl 12-hydroxydodecanoate are isolated as a light yellowish oil for a yield of 96%.

Spectroscopic Data:

IR: 3662, 2926, 2853, 1731.

$^1$H-NMR (400 MHz, CDCl$_3$): 1.05-1.25 (m, 17H), 1.40-1.60 (m, 4H), 2.17 (t, J=7.2 Hz, 2H), 2.34 (s, 1H), 3.49 (t, J=6.8 Hz, 2H), 4.01 (1, J=7.2 Hz, 2H).

$^{13}$C-NMR (75.3 MHz, CDCl$_3$): 14.0, 24.7, 25.6, 28.9, 29.0, 29.2, 29.2, 29.3, 29.4, 32.6, 34.2, 59.98, 62.6, 173.8.

MS: 234 (M$^+$)

b) Synthesis of ethyl 12-bromododecanoate

In a 100 mL two-neck flask with a reflux condenser and magnetic anchor, under a static head of nitrogen, ethyl 12-hydroxydodecanoate (1.65 g, 6.7 mmol) is dissolved in dichloromethane (20 mL). PPh$_3$ (1.93 g, 7.4 mmol) and NBS (1.6 g, 7.0 mmol) are added. The mixture is left stirring under reflux conditions for 24 hours. It is concentrated in the Rotavapor and the product is purified with column chromatography on silica gel with an eluant mixture of petroleum ether/ethyl acetate 5/1. 1.92 g (yield=92%) of ethyl 12-bromododecanoate are isolated as a light yellowish oil.

Spectroscopic Data:

IR: 2926, 2853, 1731.

$^1$H-NMR (400 MHz, CDCl$_3$): 1.20-1.45 (m, 15H), 1.55-1.65 (m, 4H), 1.80-1.90 (m, 2H), 2.30 (t, J=7.0 Hz, 2H), 3.40 (t, J=7.1 Hz, 2H), 4.10 (1, J=7.2 Hz, 2H).

$^{13}$C-NMR (75.3 MHz, CDCl$_3$): 14.2, 24.9, 28.1, 28.7, 29.1, 29.3 (2CH$_2$), 29.4, 32.8, 33.9, 34.3, 61.1, 173.8.

MS: 296 (M$^+$)

c) Synthesis of ethyl 13-(diethoxyphosphoryl)tridecanoate

In a single-neck flask with a reflux condenser, ethyl 12-bromododecanoate is weighed (1.8 g, 7.37 mmol) and triethyl phosphite (2.6 mL, 15 mmol) is added. The reaction mixture is brought to 150° C. and left stirring under a static head of nitrogen. After 24 hours the one neck balloon is attached to the high vacuum pump to eliminate volatile products and the resulting dense oil is directly loaded with column chromatography on silica gel. It is eluted with a mixture of ethyl acetate/petroleum ether 1/1 which leads to the isolation of 2.5 g (yield 94%) of ethyl 13-(diethoxyphosphoryl)tridecanoate as a colourless oil.

Spectroscopic Data:

IR: 3684, 3445, 2978, 2853, 1730, 1216, 1058.

$^1$H-NMR (400 MHz, CDCl$_3$): 1.05-1.15 (m, 25H), 1.40-1.80 (m, 4H), 2.0-2.1 (m, 2H), 4.00 (brs, 6H).

$^{13}$C-NMR (75.3 MHz, CDCl$_3$): 14.0, 15.9, 16.2 (d, J=5.6 Hz), 22.1, 22.2, 24.7, 26.2, 26.8, 29.0, 29.1, 29.2, 30.3 (d, J=16.1 Hz), 34.1, 59.9, 61.11 (d, J=6.4 Hz), 63.7 (d, J=5.6 Hz), 173.6.

MS: 364 (M$^+$)

d) Synthesis of potassium hydrogen-13-ethoxy-13-oxamidecylphosphonate

In a single-neck flask with a reflux condenser, ethyl (diethoxyphosphoryl)tridecanoate (1.3 g, 3.6 mmol) is weighed and concentrated HCl (2 mL) is added. The mixture is brought to a temperature of 100° C. and left stirring under a static head of nitrogen. After 6 days it is concentrated in the high vacuum pump. A sticky white solid is obtained. $^1$H-NMR analysis still shows the presence of the ester function. KOH is added (460 mg in 20 mL of water/MeOH 1/1) and the whole is left stirring all night at room temperature. Next morning it is dried and any organic impurities are extracted with EtOAc. The aqueous phase is concentrated, 10 mL of MeOH are added to the sticky white solid obtained and it is left under reflux conditions for 5 minutes. The solution is separated using a pipette and the solid white residue is dried under a high vacuum and characterised by spectroscopy. 800 mg (Yield=62%) of product are obtained as a powdery white solid.

m.p.=350-360° C.

Spectroscopic Data:

IR: 3411 (br), 2922, 2848, 1649, 1566, 1410, 1041, 977.

$^1$H-NMR (400 MHz, D$_2$O): 1.00-1.40 (m, 20H), 2.0 (t, J=7.6 Hz, 2H).

$^{13}$C-NMR (100.3 MHz, D$_2$O): 23.5, 24.4, 26.1, 28.7, 28.9, 31.3, 37.87 (only signals distinguishable for CH$_2$)

MS (m/z): 278/2=139 (M$^+$)

Following the same synthetic protocol, 12-hydroxyamino-12-oxododecanoic acid can be obtained.

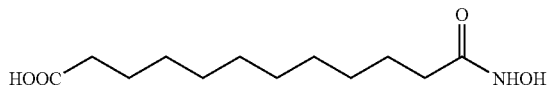

Nanoparticle/bifunctional binder complexes

Example 5

Synthesis of ethyl 12-(hydroxyamino)-12-oxododecanoate

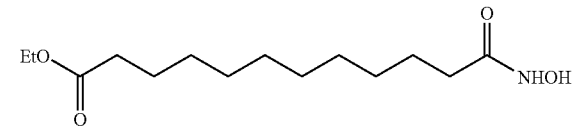

Synthesis of ethyl 12-hydroxydodecanoate

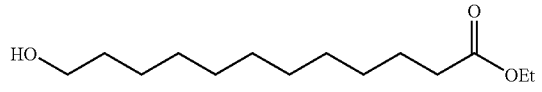 [SMILES: CCOC(=O)CCCCCCCCCCCO]

In a two-neck flask with a reflux condenser under stirring and argon flux, 12-hydroxy-dodecanoic acid, (5.0 g, 23.2 mmol), ethanol (20 mL) and acetyl chloride and acetyl chloride (0.09 ml, 1.62 mmol) are added, the mixture is refluxed for 24 h. At the end the solution is concentrated with a al rotavapor under high vacuum and the raw product is purified by column chromatography on silica gel using as eluents a mixture petrol ether/ethyl acetate 5/4. 5.45 g (yield=96%) of the desired product are isolated as a pale yellow oil.

Spectroscopic Data:

| | |
|---|---|
| $^1$H NMR δ, ppm (400 MHz, CDCl$_3$) | 1.05-1.25 (m, 17H), 1.40-1.60 (m, 4H), 2.17 (t, J = 7.2 Hz, 2H), 2.34 (s, 1H), 3.49 (t, J = 6.8 Hz, 2H), 4.01 (1, J = 7.2 Hz, 2H) |
| $^{13}$C NMR δ, ppm (100.6 MHz, CDCl$_3$) | 14.0, 24.7, 25.6, 28.9, 29.0, 29.2, 29.2, 29.3, 29.4, 32.6, 34.2, 59.98, 62.6, 173.8 |

| | |
|---|---|
| IR, cm$^{-1}$ | 3423, 2928, 2855, 1737 |
| MS | 245 (M + 1)$^+$ |

Synthesis of the 12-ethoxy-12oxodocecanoic acid

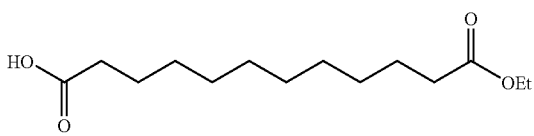 [SMILES: CCOC(=O)CCCCCCCCCCC(=O)O]

In a single-neck flask equipped with perforable sect, under argon flux and stirring, acetonitrile (80 mL) is added to periodic acid (5.13 g, 22.5 mmol) and after 15' temperature is brought to 0° C. In this condition a solution of ethyl 12-hydroxydodecanoate (5; 2.5 g, 10.2 mmol) and pyridine clorocromate (PCC; 44 mg, 0.20 mmol) in acetonitrile (20 mL) is dropped therein. After the addition reaction is carried on for 24 h at room temperature. The reaction is interrupted by addition of ethyl acetate (100 mL). The reaction solution is washed with a solution 1:1 distilled water/brine (2×50 mL), with a aqueous solution saturated in sodium hydrogensulphite (NaHSO$_3$; 2×25 mL) and brine (2×50 mL). The organic phase is anhydrified with anhydrous sodium sulphate and filtered under vacuum. The solvent is evaporated and the product is dried under high vacuum giving 2.45 g of a white solid. The product is purified by column chromatography on silica gel, eluents ethyl acetate/petrol ether 3/1. 2.1 g (Yield=80%) of the desired product are obtained as a white solid. The reaction was performed according to Hunsen, M. Synthesis 2005, 2487-2490.
Spectroscopic Data:

| | |
|---|---|
| $^1$H NMR δ, ppm (400 MHz, CDCl$_3$) | 1.26 (m, 15H), 1.61 (m, 4H), 2.28 (t, J = 7.6 Hz, 2H), 2.35 (t, J = 7.4 Hz, 2H), 4.12 (q, J = 7.1 Hz, 2H) |
| $^{13}$C NMR δ, ppm (100.6 MHz, CD$_3$OD) | 14.5, 26.0, 30.1-30.5, 34.9, 35.0, 61.3, 175.4, 177.5 |
| IR, cm$^{-1}$ | 2916, 2850, 1739, 1714, 1473, 1432 |
| MS | 259 (M + 1)$^+$ |

Synthesis of ethyl 12-(hydroxyamino)-12-oxododecanoate

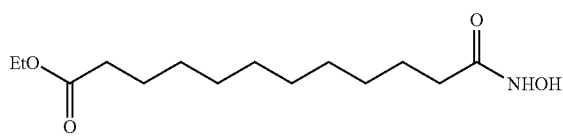

In a single-neck flask equipped with reflux condenser, under stirring and argon flux, the 12-ethoxy-12-oxododecanoic acid (13; 1.5 g, 5.8 mmol) is solved in chloroform (20 mL). Thionyle chloride is dropped (SOCl$_2$; 0.64 mL, 8.8 mmol) and the reaction is carried on under reflux for 3 h. The mixture is cooled down to room temperature and the solvent is eliminated under high vacuum. The obtained product is solved in dichloromethane (20 mL) and is added, at room temperature and under stirring, with a solution of hydroxylamine hydrochloride (0.61 g, 8.8 mmol) in pyridine (10 mL) leaving to react for 12 h under the same conditions. All the solvent are eliminated under high vacuum and the remaining product is solubilised in ethyl acetate (50 mL), washed with distilled water (3×20 mL). The organic phase is anhydrified with anhydrous sodium sulphate and filtered under vacuum. The solvent is evaporated and dried under high vacuum to give 1.3 g (Yield=82%) of product as a pale yellow solid.
Spectroscopic Data:

| | |
|---|---|
| $^1$H NMR δ, ppm (400 MHz, CD$_3$OD) | 1.27 (m, 15H), 1.60 (m, 4H), 2.08 (t, J = 7.4 Hz, 2H), 2.30 (t, J = 7.2 Hz, 2H), 4.11 (q, J = 7.1 Hz, 2H) |
| $^{13}$C NMR δ, ppm (100.6 MHz, CD$_3$OD) | 14.5, 25.9, 26.5, 30.0-30.4, 33.1, 35.0, 61.3, 173.4, 175.4 |
| IR, cm$^{-1}$ | 3421, 2922, 2848, 1735, 1636, 1469, 1421 |
| MS | 274 (M + 1)$^+$ |

Example 6

Cobalt ferrite/12-hydroxydodecyl phosphonate acid nanoparticle complexes (Product diagram 1.2)

A quantity of 10 g of a dispersion in diethylene glycol containing 3% in weight of nanoparticles, for example cobalt ferrite, with diameter 5 nm is added to 0.3 grams of 12-hydroxydodecyl phosphonate acid added after solubilisation in 20 g of lightly heated EtOH, the whole is kept stirring at room temperature for 2 hours. The specimen is then precipitated with acetone, centrifuged and separated. The specimen is then redispersed in ethanol and again precipitated, centrifuged and separated to eliminate any impurities. The wet specimen may then be redispersed in the desired solvent.

Example 7

Cobalt ferrite/12-Amino-N-hydroxydodecanamide nanoparticle complexes (Product diagram 1.2)

A quantity of 10 g of a dispersion in diethylene glycol containing 3% in weight of nanoparticles, for example cobalt ferrite, with diameter 5 nm is added to 0.21 of 12-amino-N-hydroxydodecanamide added after solubilisation in 20 g of boiling water, the whole is kept stirring at room temperature for 2 hours. The specimen is then precipitated with acetone, centrifuged and separated. The specimen is then redispersed in ethanol and again precipitated, centrifuged and separated to eliminate any impurities. The wet specimen can then be redispersed in the desired solvent.

Polymer/functional molecule inorganic nanoparticle complexes

Example 8

Synthesis of Functionalised nanoparticle Compounds with Polyamidoamine (PAA) Composed of Ethylendiamino Diacetic Acid-Bisacryloil Piperazine—Product Diagram 1.2.1

A quantity of 10 g of an aqueous dispersion containing 0.1% in weight of nanoparticles, for example cobalt ferrite, with diameter 5 nm functionalised with hydroxamic 12-aminododecanoic acid is added to 10 g of a solution containing 0.02 g of polymer. The pH is adjusted to 8 by adding a few drops of triethylene amine. The solution is left stirring in the dark at 25° C. for 2 days. The product obtained is then filtered with the Amicon filtration system to eliminate the non reacted polymer. The product may then be left in a solution or dried for characterisation analysis.

Example 9

Synthesis of the Functionalised Nanoparticle/Cyclodextrin Compound a) Procedure for Direct Fixing of Cyclodextrin on the "Grafted" Product (Product Diagram 1.2.1)

A quantity of 10 g of a dispersion in diethylene glycol containing 0.1% in weight of nanoparticles, for example cobalt ferrite, with diameter 5 nm is added to an ethanol solution containing 0.21 grams of hydroxamic 12-hydroxy-dodecanoic acid added after solubilisation in 20 g of lightly heated EtOH, the whole is kept stirring at a temperature of 60° C. for 1 hour. The specimen is then precipitated with acetone, centrifuged and separated. The solid obtained is then redispersed in ethanol and again precipitated, centrifuged and separated to eliminate any impurities. The wet specimen may then be redispersed in DMF (15 mL), dicyclohexylcarbodiimide (DCC, 2 g), 4-dimethylamino pyridine (DMAP 0.2 g) are added and the whole is cooled to 0° C. The α-cyclodextrin carboxylic acid (6-deoxy-6-carboxy-α-cyclodextrin, 1 g) is suspended in DMF (25 mL). It is cooled to 0° C. and slowly added to the reaction mixture. It is left stirring for 48 hours at room temperature. The solution is poured into acetone (100 mL) and the precipitate that forms is separated and dried under a high vacuum. The crude product may be further purified with Sephadex CM-25.

b) Procedure for Direct Fixing of Cyclodextrin on the Functional Binder and Subsequent Grafting on Cobalt Ferrite. (Product Diagram 1.4)

To a solution of 6-deoxy-6-carboxy-α-cyclodextrin (1 g, 0.87 mmol) in $H_2O$/EtOH 1/1 (20 mL) are added DCC (197 mg, 0.96 mmol), DMAP (12 mg, 0.087 mmol, 10% catalytic) and hydroxamic 12-hydroxy dodecanoic acid (0.2 g, 0.87 mmol).

The reaction mixture is left stirring for 72 hours at room temperature. The crude product is purified with Sephadex CM-25, obtaining 360 mg (30%) of cyclodextrin bound to hydroxamic 12-hydroxy dodecanoic acid.

A quantity of 200 mg of the obtained product is solubilised in 20 ml of 96% ethanol and added to 10 ml of a dispersion in diethylene glycol containing 0.1% in weight of nanoparticles of cobalt ferrite with diameter 5 nm. The mixture is left stirring for 2 hours at room temperature. The specimen is then precipitated with acetone, centrifuged and separated. The specimen is then redispersed in ethanol and again precipitated, centrifuged and separated to eliminate any impurities. The specimen can then be re-dispersed in the desired solvent.

The invention claimed is:
1. Complexes consisting of metal oxides, iron, cobalt or their alloys in nanoparticle form and a difunctional compound, wherein the difunctional compound is ethyl 12-(hydroxyamino)-12-oxododecanoate.
2. Complexes according to claim 1 wherein said metal oxides in nanoparticle form are compounds with the formula:

in which $M^{II}$=Co, Ni, $Fe^{II}$, Zn, Mn and
$M^{III}$=$Fe^{III}$, Co, Al.
3. Complexes according to claim 1, wherein said metal oxides are selected from the group consisting of: cobalt ferrite $CoFe_2O_4$, magnetite $FeFe_2O_4$, maghemite $Fe_2O_3$ and any combinations thereof.
4. A complex that is nanoparticle Cobalt ferrite/12-Amino-N-hydroxy dodecanamide.

* * * * *